United States Patent [19]

Matsutani

[11] Patent Number: 4,799,311

[45] Date of Patent: Jan. 24, 1989

[54] APPARATUS FOR ATTACHING SUTURE TO SURGICAL NEEDLE

[75] Inventor: Kanji Matsutani, Tochigi, Japan

[73] Assignee: 501 Matsutani Seisakusho Co., Ltd., Tochigi, Japan

[21] Appl. No.: 159,212

[22] Filed: Feb. 23, 1988

[30] Foreign Application Priority Data

Feb. 26, 1987 [JP] Japan .................. 62-41389

[51] Int. Cl.$^4$ ...................... B21D 39/00; B41G 1/06
[52] U.S. Cl. ...................... 29/209; 72/448; 163/1
[58] Field of Search .............. 29/407, 517, 709, 713, 29/714, 715, 720; 72/416, 434, 452, 448; 163/1,5

[56] References Cited

U.S. PATENT DOCUMENTS

| | | | |
|---|---|---|---|
| 4,060,885 | 12/1977 | Hoffman et al. | 29/517 X |
| 4,306,443 | 12/1981 | Matsutani | 72/434 |
| 4,722,384 | 2/1988 | Matsutani | 72/448 X |

FOREIGN PATENT DOCUMENTS

GBA1563074 4/1977 United Kingdom .

*Primary Examiner*—Timothy V. Eley
*Attorney, Agent, or Firm*—Wegner & Bretschneider

[57] ABSTRACT

An apparatus for attaching an end of a suture to an axially extending bore formed in a proximal end of a surgical needle. At least one of a pair of staking dies is movable toward and away from the other. A proximal end face of the surgical needle is engageable with a stopper surface of a guide unit to axially position the surgical needle. The guide unit has a guide passage extending substantially perpendicularly to the stopper surface, for guiding the end of the suture. An outlet of the guide passage opens to the stopper surface in confronting relation to a space between the staking dies. The guide passage has a tapered portion decreasing in cross-sectional area toward the outlet. The proximal end of the surgical needle is positioned by a positioning mechanism perpendicularly to the axis of the surgical needle so that the bore in the surgical needle is brought substantially into alignment with the outlet of the guide passage.

16 Claims, 6 Drawing Sheets

Fig. 1 (PRIOR ART)
Fig. 2 (PRIOR ART)
Fig. 3 (PRIOR ART)
Fig. 4 (PRIOR ART)
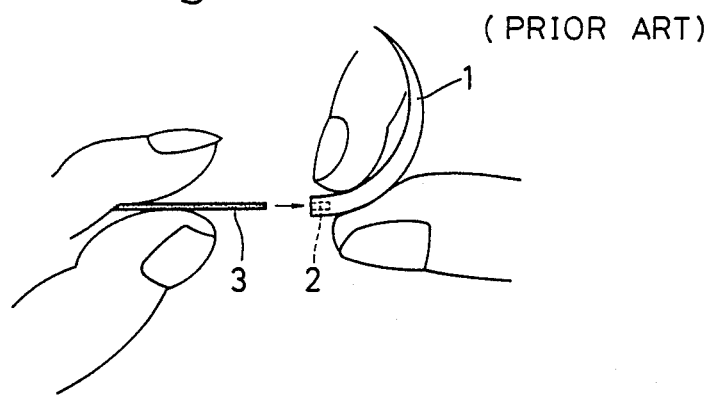
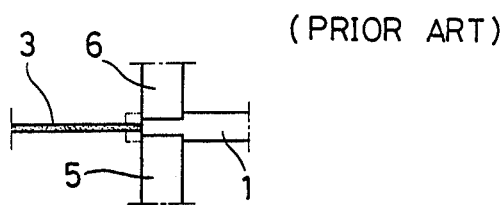
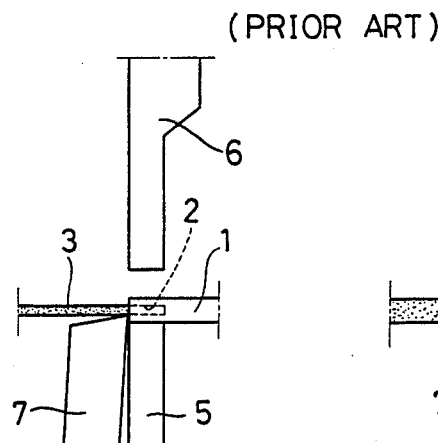
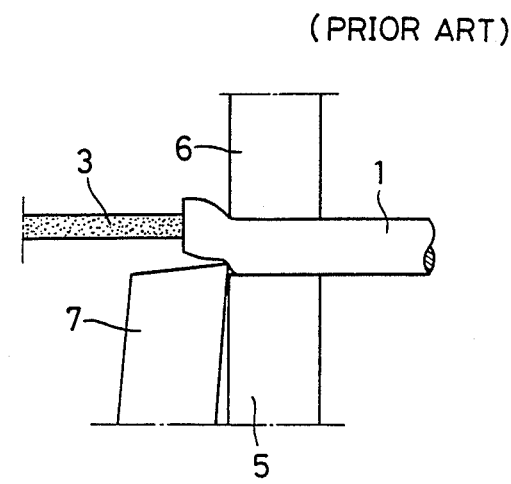

APPARATUS FOR ATTACHING SUTURE TO SURGICAL NEEDLE

BACKGROUND OF THE INVENTION

The present invention relates to an apparatus for attaching a suture to a surgical needle of eyeless type.

Hitherto, as shown in FIG. 1, when a suture 3 is to be attached to a surgical needle 1 of eyeless type, an operator has the suture 3 with his one hand, and the surgical needle 1 with his other hand. The operator inserts an end of the suture 3 into a bore 2 which is formed in a proximal end of the surgical needle 1 and which extends along an axis of the surgical needle 1. The surgical needle 1 having the suture 3 inserted into the bore 2 is then set between a pair of lower and upper staking dies 5 and 6 as shown in FIG. 2. The upper staking die 6 is moved toward the lower staking die 5 to stake the proximal end of the surgical needle 1, thereby attaching the suture 3 to the surgical needle 1.

The above-described attaching method has the following problems. First, since the surgical needle 1 and the suture 3 are extremely fine in diameter, considerable skill is required for the operation of insertion of the suture 3 into the bore 2 of the surgical needle 1. In addition, the inserting operation overworks the operator's eyes, making it difficult to continue the inserting operation for a long period of time.

Secondly, since the axial position of the surgical needle 1 is measured with the eye, it is difficult to position the surgical needle 1 correctly. Specifically, as indicated by the phantom lines in FIG. 2, staking might be carried out with the proximal end of the surgical needle 1 protruding considerably from the staking dies 5 and 6, resulting in defective products.

In order to dissolve the above second problem, an apparatus has been developed as shown in FIG. 3, which is provided with a stopper 7. The stopper 7 is arranged beside the lower staking die 5, and has an upper end protruding from the lower staking die 5. The protruding height of the upper end of the stopper 7 is less than a thickness of a peripheral wall of the surgical needle 1 surrounding the bore 2, in order not to prevent insertion of the suture 3. The proximal end face of the surgical needle 1 is abutted against the stopper 7 so that the surgical needle 1 is positioned axially. However, the following problem might occur in the apparatus shown in FIG. 3. That is, since the height of the upper end of the stopper 7 protruding from the lower staking die 5 is very small, the proximal end of the surgical needle 1 might run on to the stopper 7. If the surgical needle 1 is staked by the staking dies 5 and 6 with the proximal end of the surgical needle 1 running on to the stopper 7, a staking defect would occur as shown in FIG. 4.

The apparatuses illustrated in FIGS. 2 through are disclosed, for example, in Japanese Patent Publication Nos. 56-43420 and 57-56412, Japanese Utility Model Publication Nos. 57-10646, 61-88564 and 62-4345, U.S. Pat. No. 4,306,443 corresponding to the abovementioned Japanese Patent Publication No. 57-56412, U.S. Pat. No. 4,722,384 issued on Feb. 2, 1988, and the like. The above-noted patents have all been filed in the name of the assignee of this application.

SUMMARY OF THE INVENTION

It is an object of the invention to provide an apparatus for attaching a suture to a surgical needle, which can ensure axial positioning of the surgical needle, and which facilitates insertion of the suture into an axially extending bore formed in a proximal end of the surgical needle.

According to the invention, there is provided an apparatus for attaching an end of a suture to a bore formed in a proximal end of a surgical needle and extending along an axis of the surgical needle, the apparatus comprising:

a pair of staking dies, at least one of the staking dies being movable toward and away from the other staking die;

guide means arranged adjacent a side surface of at least the other staking die, the guide means having a stopper surface with which a proximal end face of the surgical needle is engageable to position the surgical needle in a direction along the axis thereof, the guide means having a guide passage extending substantially perpendicularly to the stopper surface, for guiding the end of the suture, the guide passage having an inlet and an outlet, the outlet opening to the stopper surface in confronting relation to a space between the staking dies, the guide passage being provided with a tapered portion having a cross-sectional area decreasing toward the outlet; and positioning means for positioning the proximal end of the surgical needle in a direction perpendicular to the axis of the surgical needle so as to bring the bore in the proximal end of the surgical needle substantially into alignment with the outlet of the guide passage of the guide means.

BRIEF DESCRIPTION OF THE DRAWINGS

FIG. 1 is a perspective view showing a known method of inserting an end of a suture into an axially extending bore formed in a proximal end of a surgical needle;

FIG. 2 is a fragmental side elevational view of a conventional staking apparatus;

FIG. 3 is a fragmental side elevational vie of another conventional staking apparatus;

FIG. 4 is an enlarged fragmental side elevational view or the apparatus illustrated in FIG. 3;

DETAILED DESCRIPTION

Figure 5:
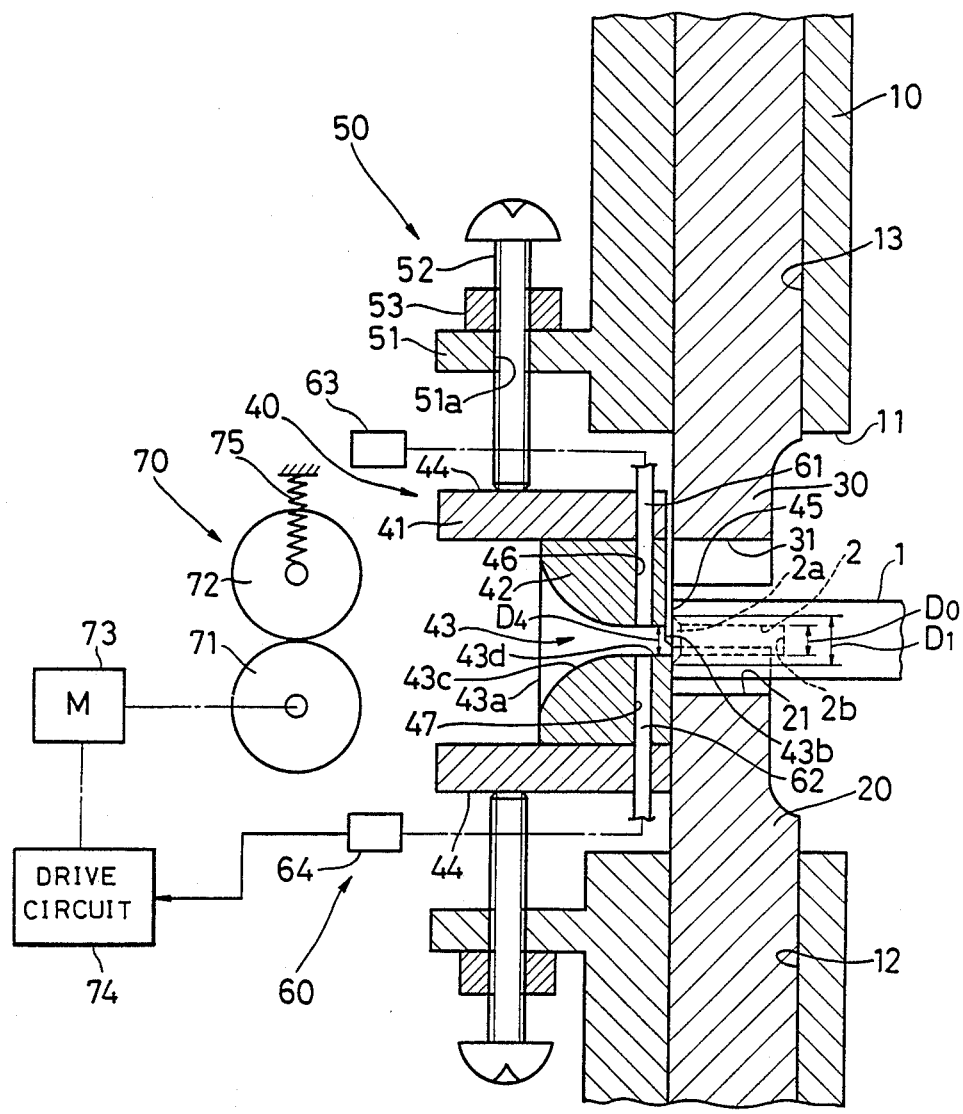
FIG. 5 is a cross-sectional view of a suture attaching apparatus according to an embodiment of the invention.

Referring first to FIGS. 5 through 10, there is shown an attaching apparatus according to an embodiment of the invention. A surgical needle 1 employed in the embodiment will previously be described. A bore 2 having an open end and a closed end 2b is formed in a proximal end of the surgical needle 1 and extends along an axis thereof. The bore 2 has, adjacent its open end, a tapered portion 2a diverging away from the closed end 2b. The remaining portion of the bore 2 except for the tapered portion 2a has a diameter $D_0$, and the open end of the bore 2 has a diameter $D_1$. The diameter $D_0$ is slightly larger than a diameter $D_2$ of an end of a suture 3 (see FIG. 8) to be inserted into the bore 2 of the surgical needle 1.

Figure 6:
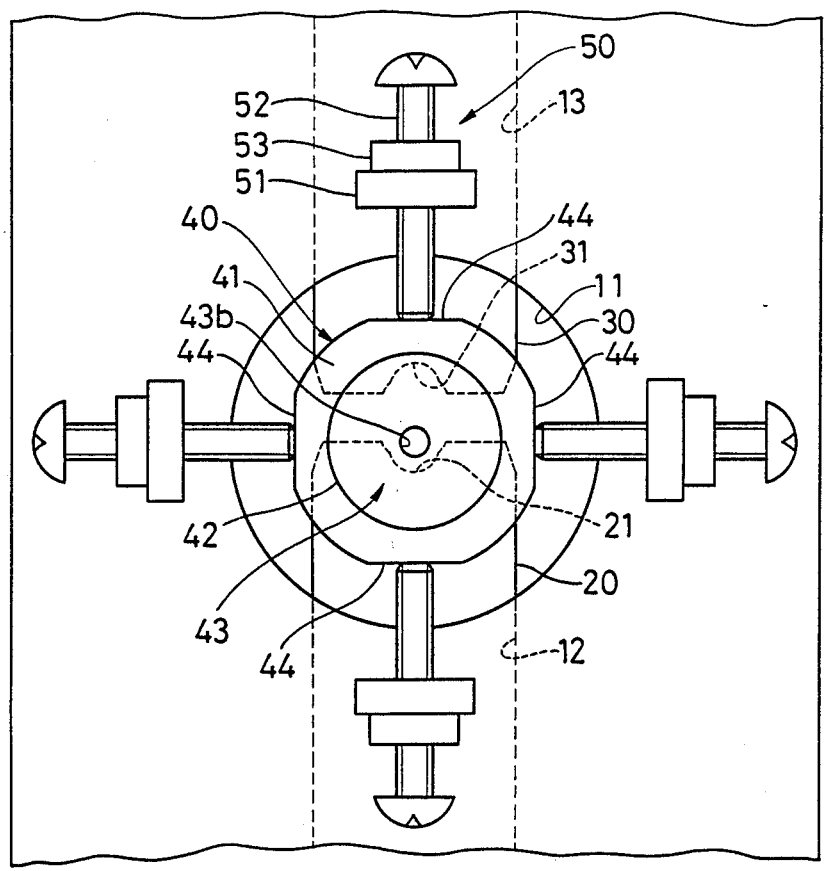
FIG. 6 is a front elevational view of the apparatus illustrated in FIG. 5.
Figure 7:
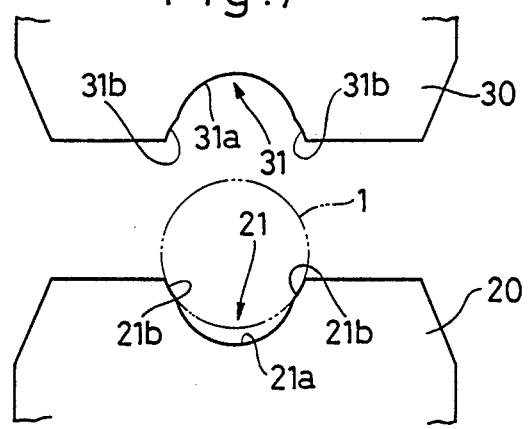
FIG. 7 is an enlarged front elevational view of a pair of staking dies illustrated in FIG. 5.

As shown in FIG. 5 and 6, the attaching apparatus comprises a stationary base frame 10 formed therein with a central opening 11 in the form of a circle and a pair of channels 12 and 13 each having a rectangular cross-sectional shape. The channels 12 and 13 extend vertically and are aligned with each other. The channels 12 and 13 have their respective one ends which open to the central opening 11.

The attaching apparatus comprises a pair of lower and upper staking dies 20 and 30. The lower staking die 20 is formed by an elongated member having a rectangular cross-sectional shape. The lower staking die 20 is accommodated in the channel 12 and is fixed to the base frame 10. The upper staking die 30 has the same cross-sectional shape as the lower staking die 20, and is received in the channel 13 for sliding movement therealong. The upper staking die 30 is so designed as to be moved toward and away from the lower staking die 20 by a moving mechanism (not shown). The moving mechanism is known from the above-mentioned patents, and the description of the moving mechanism will therefore be omitted. The staking dies 20 and 30 have their respective forward ends which are confronted with each other and which project into the opening 11. A recess 21 having a generally semi-circular cross-section is formed in the forward end of the staking die 20 and, likewise, a recess 31 having a generally semi-circular cross-section is formed in the forward end of the staking die 30. As clearly shown in FIG. 7, the recess 21 has a central portion 21a and opposite side portions 21b and 21b, and the recess 31 has a central portion 31a and opposite side portions 31b and 31b. Each of the central portions 21a and 31a of the respective recesses 21 and 31 has a radius of curvature less than that of the outer periphery of the proximal end of the surgical needle 1. Each of the side portions 21b and 31b has a radius of curvature equal to or slightly larger than that of the outer periphery of the proximal end of the surgical needle 1.

A guide unit 40 for guiding the suture 3 (see FIG. 8) is arranged on the left-hand side of the staking dies 20 and 30 as viewed in FIG. 5. The guide unit 40 is composed of a cylindrical member 41 and a columnar guide member 42 which has a circular cross-section and which is fixedly accommodated in the cylindrical member 41. The guide member 42 has axial one end face confronted with the staking dies 20 and 30. A lower half portion of the axial one end face of the guide member 42 serves as a stopper surface 45 having a function subsequently to be described. The lower half portion of the axial end face of the guide member 42 and a lower half portion of a corresponding axial end face of the cylindrical member 41 are in contact with the left-hand end face of the lower staking die 20 as viewed in FIG. 5. An upper half portion of the axial one end face of the guide member 42 and an upper half portion of the corresponding axial end face of the cylindrical member 41 are spaced apart slightly away from the upper staking die 30, in order to prevent friction contact with the left-hand end face of the upper staking die 30 during movement thereof toward and away from the lower staking die 20. The end face of the guide member 42, which is confronted with the staking dies 20 and 30, may be even or flush over the entire area to form a stopper surface spaced apart slightly away from the pair of staking dies 20 and 30. In addition, the end face of the cylindrical member 41, which is confronted with the staking dies 20 and 30, may be flush with the end face of the guide member 42 as shown in FIG. 5, or may be spaced from the end face of the guide member 42 away from the staking dies 20 and 30.

The guide member 42 is formed therein with a guide passage 43 having an inlet 43a remote from the stopper surface 45 and an outlet 43b adjacent the stopper surface 45. The guide passage 43 has an axis which is in conformity with an axis of the guide member 42 and which extends perpendicularly to the stopper surface 45. The guide passage 43 is circular in cross-section at any point along its axis, and has a portion 43c which is tapered in such a fashion that the guide passage 43 is gradually reduced in diameter from the inlet 43a toward the outlet 43b. The guide passage 43 also has a straight portion 43d which is equal in diameter over its entire length and which extends through a predetermined length adjacent the outlet 43b. The straight portion 43d may be tapered in an extremely gentle manner. The tapered portion 43c is steep in gradient in a section adjacent the inlet 43a, and becomes gradually gentle in gradient as a distance from the inlet 43c increases, so that the tapered portion 43c merges smoothly to the straight portion 43d. Thus, the guide passage 43 has a shape resembling a trumpet. A diameter $D_4$ of the outlet 43b, that is, a diameter of the straight portion 43d is equal to or larger than the diameter $D_2$ of the end of the suture 3 (see FIG. 8), but is equal to or smaller than the diameter $D_1$ of the open end of the bore 2 in the surgical needle 1. The diameter $D_4$ of the outlet 43b is preferably on the same order as the diameter $D_0$ of the portion of the bore 2 except for the tapered portion 2a, but may be larger or smaller than the diameter $D_0$ of the bore 2 provided that the above conditions are satisfied. If the tapered portion 2a as describe above is not formed at the open end of the bore 2, the diameter $D_4$ of the outlet 43b is required to be equal to or smaller than the diameter $D_0$ of the bore 2.

The guide unit 40 is supported by a support mechanism 50 so as to be adjustable in position. Specifically, four flanges 51 each having therein a threaded bore 51a are formed on the left-hand end face of the base frame 10 as viewed in FIG. 5, in circumferentially equidistantly spaced relation to each other about the opening 11. Four bolts 52 are threadedly engaged respectively with the threaded bores 51a of the flanges 51. The bolts 52 have their respective forward ends which are abutted respectively against four planar surfaces 44 formed on the outer periphery of the cylindrical member 41 in circumferentially equidistantly spaced relation to each other. Adjustment in position of the bolts 52 with respect to the respective flanges 51 makes it possible to adjust the guide unit 40 to its reference position where, when positioning of the surgical needle 1 is made such that the proximal end of the surgical needle 1 is set in the recess 21 of the lower staking die 20 subsequently to be described, the axis of the bore 2 in the surgical needle 1 is brought into conformity with the axis of the guide passage 43. Lock nuts 53 are beforehand threadedly engaged respectively with the bolts 52. Subsequent to the above-described adjustment in position of the guide unit 40, the lock nuts 53 are tightened respectively against the flanges 51 to prevent inadvertent angular movement of the bolts 52 about their respective axes, thereby keeping the guide unit 40 at its adjusted position.

Associated with the guide unit 40 is a detecting system 60 for detecting passage of the suture through the guide passage 43. The detecting system 60 comprises a pair of optical fibers 61 and 62, a light emitting element 63 optically connected to one end of the optical fiber 61, and a light receiving element 64 optically connected to one end of the optical element 62. The guide unit 40 is provided therein with a pair of bores 46 and 47 having their respective axes which extend perpendicularly to the axis of the guide passage 43 and which are aligned with each other. The bores 46 and 47 have their respective one ends which open to the straight portion 43d of the guide passage 43. The other ends of the respective optical fibers 61 and 62 are fixedly fitted respectively into the bores 46 and 47 such that the other ends of the respective optical fibers 61 and 62 are confronted with each other through the straight portion 43d of the guide passage 43.

A suture feed device 70 is arranged on the opposite side of the guide unit 40 from the staking dies 20 and 30. The suture feed device 70 comprises a pair of rollers 71 and 72, and a motor 73 drivingly connected to the roller 71. The roller 72 is biased toward the roller 71 under resilient force of a spring 75. The motor 73 is electrically connected to a drive circuit 74 which is operative in response to a detecting signal from the light receiving element 64 to control driving of the motor 73.

Figure 8:
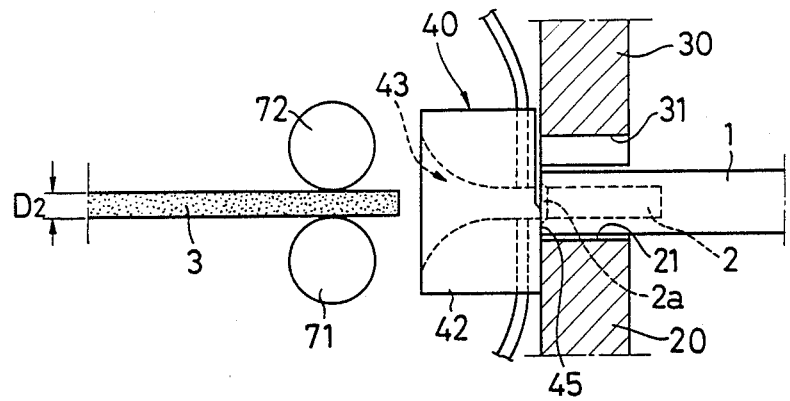
FIGS. 8 through 10 are views for explanation, in due order, of operation of attaching a suture to a surgical needle by the use of the apparatus shown in FIGS. 5 through 7.

In the attaching apparatus constructed as described above, when the upper staking die 30 is in the position spaced upwardly from the lower staking die 20, the surgical needle 1 is inserted from the right as viewed in FIG. 8, into a space defined between the recesses 21 and 31 in the respective staking dies 20 and 30, until the proximal end face of the surgical needle 1 is abutted against the stopper surface 45 of the guide unit 40. This makes it possible to ensure axial positioning of the proximal end of the surgical needle 1. Insertion of the surgical needle 1 into the space between the recesses 21 and 31 may be carried out with the surgical needle 1 held with the operator's hand. Alternatively, a needle moving mechanism may be employed in such a manner that the surgical needle 1 clamped by a chuck of the needle moving mechanism, and the chuck having carried thereon the surgical needle 1 is moved axially to insert the surgical needle 1 into the space defined between the recesses 21 and 31. If insertion of the surgical needle 1 is carried out with the operator's hand, the proximal end of the surgical needle 1 is first placed on the opposite side portions 21b and 21b of the recess 21 in the lower staking die 20 as indicated by the phantom lines in FIG. 7, to thereby determine the position of the proximal end of the surgical needle 1 in the direction perpendicular to the axis of the surgical needle 1. This brings the axis of the bore 2 into alignment with the axis of the guide passage 43 in the guide unit 40. Also in case where insertion of the surgical needle 1 is carried out by the use of the needle moving mechanism, the surgical needle 1 can be positioned in a manner like that of the above-described manual insertion, if the surgical needle 1 is moved downwardly after having been axially moved, to bring the surgical needle 1 into abutment against the opposite side portions 21b and 21b of the recess 21 in the lower staking die 20.

Figure 9:
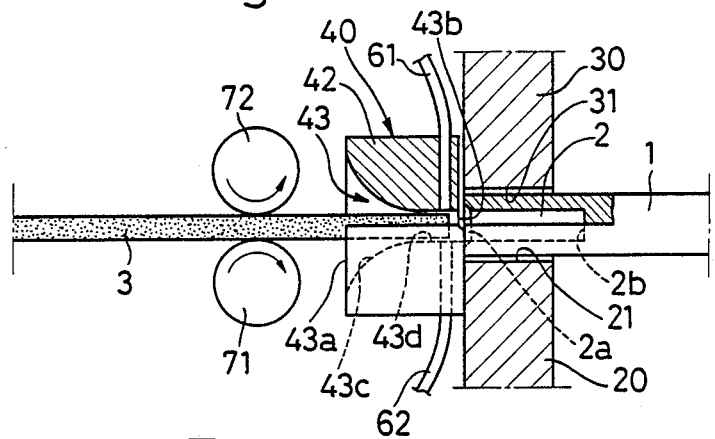

Subsequently, as shown in FIG. 9, the upper staking die 30 is moved downwardly under a weak spring force, to lightly clamp the surgical needle 1 between both the staking dies 20 and 30, whereby the proximal end of the surgical needle 1 is maintained accommodated in the recesses 21 and 31 of the respective staking dies 20 and 30. On this occasion, the proximal end of the surgical needle 1 is supported in such a state that the proximal end of the surgical needle 1 is abutted against four locations including the opposite side portions 21b and 21b of the recess 21 and the opposite side portions 31b and 31b of the recess 31.

It is supposed that in the inserting operation of the surgical needle 1 into the space between the recesses 21 and 31 of the respective staking dies 20 and 30, the surgical needle 1 is only moved axially by the needle moving mechanism, but is not moved downwardly. Then, positioning of the proximal end of the surgical needle 1 in the direction perpendicular to the axis of the surgical needle 1 is completed for the first time when the proximal end of the surgical needle 1 is clamped between the upper and lower staking dies 20 and 30.

After the upper staking die 30 is moved down to lightly hold the surgical needle 1 down to the lower staking die 20, the motor 73 is driven to rotate the rollers 71 and 72, thereby feeding the end of the suture 3 into the guide passage 43 of the guide unit 40. When the end of the suture 3 is fed in this manner, even if the axis of the end of the suture 3 is slightly in misalignment with the axis of the guide passage 43, that is, the axis of the bore 2 in the surgical needle 1, the end of the suture 3 is guided by the tapered portion 43c of the guide passage 43 adjacent the inlet 43a thereof, toward the outlet 43b, so that the end of the suture 3 can be guided by the guide passage 43 into the bore 2 of the surgical needle 1 which is aligned with the axis of the guide passage 43. Thus, the end of the suture 3 can easily be inserted into the bore 2 of the surgical needle 1, thereby enabling automatic feeding of the suture 3 by the suture feed device 70.

In addition, the straight portion 43d provided adjacent the outlet 43b can assist that the end of the suture 3 drawn out of the guide passage 43 maintains lineality substantially in conformity with the axis of the guide passage 43. Accordingly, if the end of the suture 3 is slightly caught by the inner peripheral wall surface of the bore 2, the end of the suture 3 is prevented from being bent. Thus, it can be ensured that the end of the suture 3 is smoothly inserted into the bore 2.

Further, the tapered portion 2a at the forward end of the bore 2 guides the end of the suture 3, thereby making it possible to smoothly feed the end of the suture 3 toward the closed end 2b of the bore 2.

Since the diameter $D_4$ of the outlet 43b of the guide passage 43 is smaller than the diameter $D_1$ of the open end of the bore 2 enlarged by the tapered portion 2a, it can be ensured to feed the end of the suture 3 into the bore 2, even if an error is present in the adjustment in position of the guide unit 40 so that the axis of the guide passage 43 is misaligned with the axis of the bore 2 in the surgical needle 1 by a slight amount. An allowable value of the misaligned amount is equal to or less than a difference between the radius $D_1/2$ of the open end of the bore 2 and the radius $D_4/2$ of the outlet 43b of the guide passage 43.

As the end of the suture 3 reaches the straight portion 43d of the guide passage 43 as shown in FIG. 9, the end of the suture 3 intercepts the light from the optical fiber 61 to the optical fiber 62, so that the light receiving element 64 is switched from a light-received state to a light-unreceived state. This switching signal serves as a signal representative of passage of the end of the suture 3 and is sent to the drive circuit 74. A timer incorporated in the drive circuit 74 is set in response to the signal from the light receiving element 64. After the elapse of time set by the timer, the drive circuit 74 interrupts supply of electric power to the motor 73. The time set by the timer is beforehand determined so as to be brought to the quotient obtained when a distance from the optical fibers 61 and 62 to the closed end 2b of the bore 2 is divided by the feed speed of the suture 3. Thus, it can be ensured that the end of the suture 3 is fed until it reaches the closed end 2b of the bore 2 or a location adjacent the closed end 2b.

Figure 10:
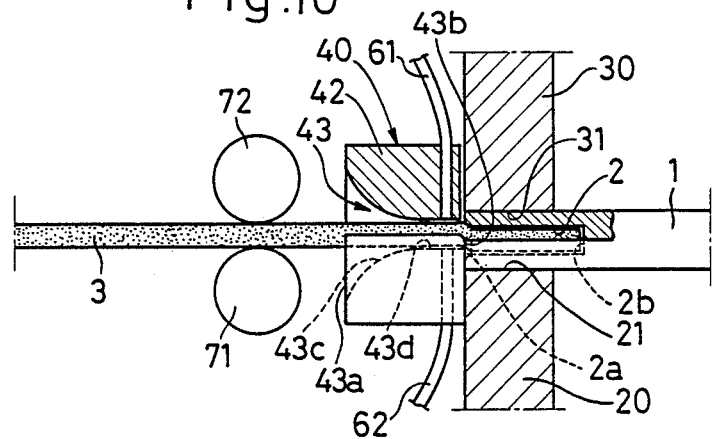

After the above-described feeding of the suture 3 has been completed, the upper staking die 30 is moved downwardly under a strong force as shown in FIG. 10, to stake the proximal end of the surgical needle 1. During this staking, the proximal end of the surgical needle 1 is moved downwardly while being deformed. By this reason, the axis of the bore 2 is deviated downwardly from the center of the outlet 43d of the guide passage 43.

Subsequently, the upper staking die 30 is brought to such a state that the upper staking die 30 is biased toward the lower staking die 20 under the weak spring force. Then, the surgical needle 1 is angularly moved about its own axis through 90 degrees, while slightly raising the upper staking die 30. Thereafter, the upper staking die 30 is again moved downwardly to press the proximal end of the surgical needle 1 against the lower staking die 20 under the strong force, thereby staking the proximal end of the surgical needle 1.

The above-described first and second stakings cause the end of the suture 3 to be fixedly secured to the bore 2 of the surgical needle 1. Thus, staking is completed. By this staking, the proximal end of the surgical needle 1 is reduced in diameter, and is brought to a radius just equal to the radii of curvature of the respective central portions 21a and 31a of the recesses 21 and 31. Thus, the proximal end of the surgical needle 1 is accommodated in a space defined by the central portions 21a and 31a of the respective recesses 21 and 31. In addition, at completion of the staking, the axis of the bore 2 is displaced from the center of the outlet 43d of the guide passage 43 by a distance equal to one half of the difference between the diameter of the proximal end of the surgical needle 1 before being staked and the diameter of the proximal end of the surgical needle 1 after having been staked.

Subsequently, the upper staking die 30 is moved upwardly away from the surgical needle 1. The surgical needle 1 is then moved horizontally away from the guide unit 40, to cause the entire length of the suture 3 to pass through the guide passage 43.

The invention should not be limited to the above-described specific embodiment, but various changes, modifications and variations may be made to the invention. For example, both the pair of staking dies may be movable such that the staking dies are moved toward the proximal end of the surgical needle positioned by the needle moving mechanism in the direction perpendicular to the axis of the surgical needle, to stake the proximal end of the needle.

Figure 11:
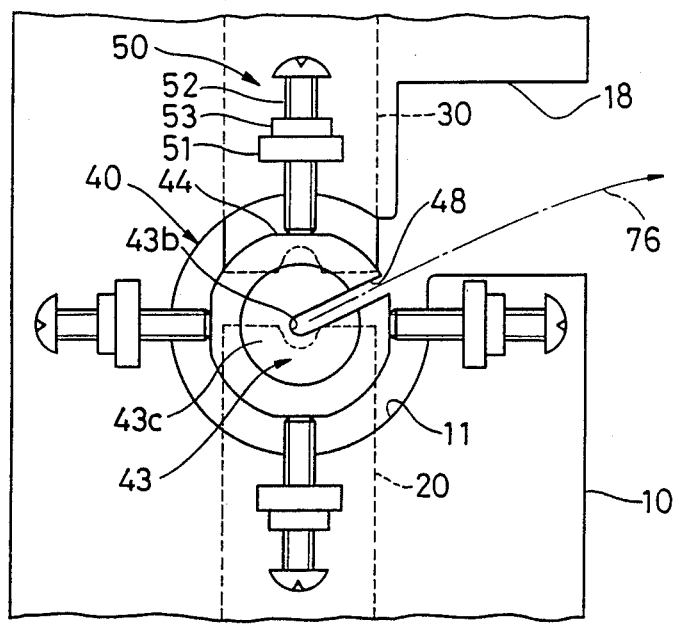
FIG. 11 is a front elevational view showing an attaching apparatus according to another embodiment of the invention.

FIG. 11 shows another embodiment of the invention. The embodiment illustrated in FIG. 11 is similar in fundamental structure to the embodiment shown in FIGS. 5 through 10. Accordingly, in FIG. 11, like or similar reference numerals are used to designate components and parts like or similar to those shown in FIGS. 5 through 10, and the detailed description of such like or similar components or parts will therefore be omitted. The embodiment shown in FIG. 11 is different from the embodiment illustrated in FIGS. 5 through 10 in that the guide unit 40 is formed therein with a radial slit 48 in communication with the guide passage 43, and the base frame 10 is formed therein with a cut-out 18 in communication with the opening 11. In the arrangement of the embodiment illustrated in FIG. 11, after staking of the surgical needle 1 has been completed, the surgical needle 1 and the suture 3 fixedly attached thereto are moved in a direction perpendicular to the axis of the guide passage 43 as indicated by the arrow 76 in such a manner that the suture 3 moves laterally along the slit 48. Thus, the suture 3 can be taken out of the guide passage 43. Accordingly, it is not required that the entire length of the suture 3 is caused to pass through the guide passage 43, thereby ensuring to prevent the suture 3 from being damaged.

A multifilament suture is often employed as the suture 3. In case of such multifilament suture, only the end of the suture is reduced in diameter and is hardened. The embodiment illustrated in FIG. 11 is particularly suitable for such multifilament suture. Specifically, since it is not required to cause the entire length of the suture to pass through the guide passage 43, the diameter of the outlet 43d of the guide passage 43 can be reduced to a small size sufficiently to permit only the diameter-reduced end of the suture to pass through the outlet 43d.

Figure 12:
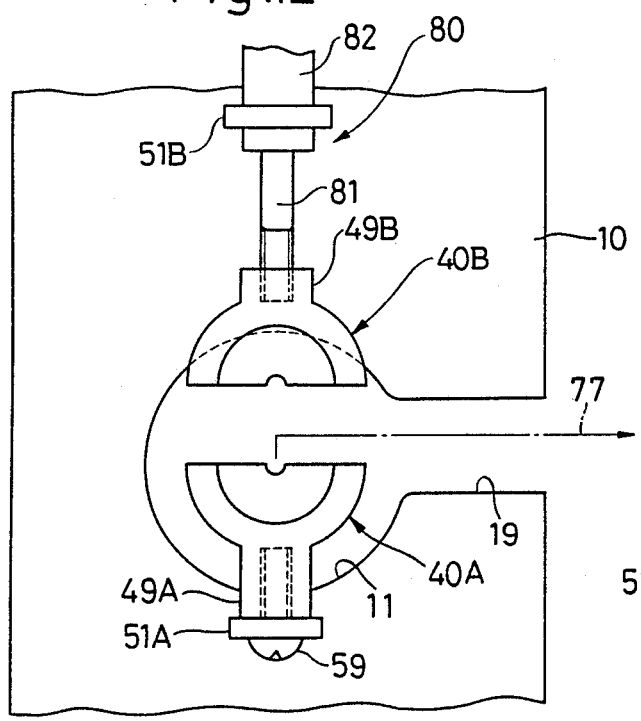
FIG. 12 is a front elevational view showing an attaching apparatus according to still another embodiment of the invention, with a pair of staking dies omitted from illustration for convenience.
Figure 13:
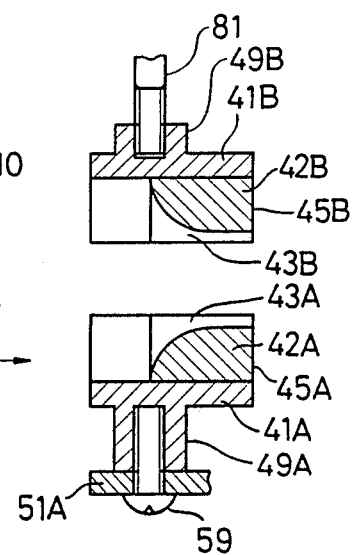
FIG. 13 is a cross-sectional view showing a guide unit of the apparatus illustrated in FIG. 12.

FIGS. 12 and 13 show still another embodiment of the invention, in which the guide unit is composed of a pair of half-split components 40A and 40B. These components 40A and 40B comprise respective semi-cylindrical members 41A and 41B and respective columnar guide members 42A and 42B each having a semi-circular cross-sectional shape. The guide members 42A and 42B are fixedly secured respectively to inner peripheral wall surfaces of the respective semi-cylindrical members 41A and 41B. The guide members 42A and 42B are provided therein with their respective guide passages 43A and 43B each having a semi-circular cross-sectional shape. When the components 40A and 40B are brought into engagement with each other, the guide passages 43A and 43B cooperate with each other to form a guide passage having a configuration in conformity with that of the guide passage 43 in the embodiment described with reference to FIGS. 5 through 10. The guide members 42A and 42B have their respective end faces which are confronted with the opening 11 of the base frame 10 and which are flush with each other. The end faces of the respective guide members 42A and 42B serve respectively as stopper surfaces 45A and 45B. The lower component 40A has a boss 49A projecting downwardly from a lower side of the semi-cylindrical member 41A. The boss 49A is fixedly mounted to a flange 51A formed on the base frame 10, by means of a screw 59. The upper component 40B has also a boss 49B projecting upwardly from an upper side of the semicylindrical member 41B. A piston rod 81 of a pneumatic actuator 80 has a forward end which is screwed into the boss 49B and which is fixedly secured thereto. The pneumatic actuator 80 has a cylinder 82 which is fixedly mounted to a flange 51B formed on the base frame 10. The base frame 10 is formed therein with a laterally extending cut-out 19 in communication with the opening 11.

In the arrangement illustrated in FIGS. 12 and 13, before the end of the suture 3 is inserted into the bore 2 of the surgical needle 1, the pneumatic actuator 80 is operated to move the upper component 40B toward the lower component 40A until the upper component 40B is brought into engagement with the lower component 40A, to form the guide passage having a circular cross-section by both the guide passages 43A and 43B. After completion of staking in a manner like that described above with reference to the embodiment shown in FIGS. 5 through 10, the upper component 40B is moved upwardly and is disengaged from the lower component 40A. With the upper component 40B disengaged from the lower component 40A, the surgical needle 1 and the suture 3 fixedly attached thereto are moved laterally along the cut-out 19 in a direction perpendicular to the axis of the surgical needle 1 as indicated in the arrow 77 in FIG. 12, so that the surgical needle 1 having fixedly attached thereto the suture 3 is taken out of the cut-out 19. Thus, advantages similar to those of the embodiment illustrated in FIG. 11 can be achieved also by the arrangement shown in FIGS. 12 and 13.

Figure 14:
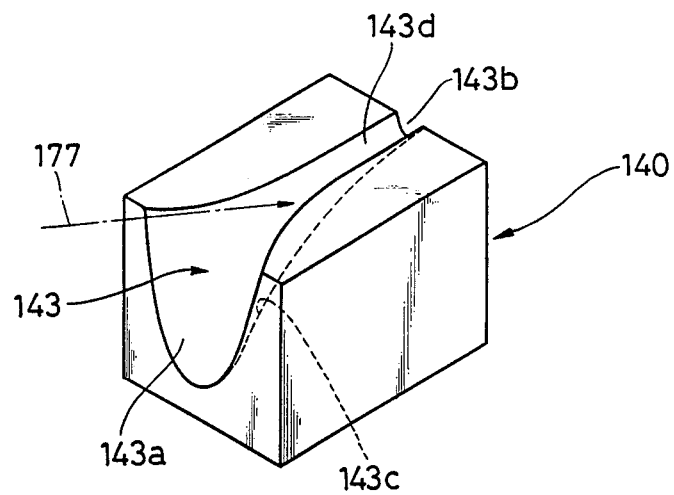
FIG. 14 is a perspective view showing a modification of a guide member.

FIG. 14 shows a guide member 140 which can be utilized in substitution for each of the guide units used in the previously described embodiments. The guide member 140 is a rectangular parallelopiped in shape, and is formed therein with a guide passage 143 having a generally U-shaped cross-section. The guide passage 143 has a tapered portion 143c gradually reduced in gradient from an inlet 143a toward an outlet 143b, and a straight portion 143d which extends through a predetermined length adjacent the outlet 143b and which is substantially equal in cross-sectional shape over the entire length. In the arrangement employing the guide member 140, the suture is fed from an obliquely upward position into the guide passage 143, as indicated by the arrow 177, in order to prevent the suture from floating up from the straight portion 143d. It is also possible for the arrangement employing the guide member 140 to take the suture attached to the surgical needle out of the guide passage 143 in a direction perpendicular to the axis of the suture, like the embodiments illustrated respectively in FIG. 11 and FIGS. 12 and 13.

In addition to the cross-sectional shape of the guide passage of each of the aforesaid embodiments, the guide passage may have a square, elliptical, V-shaped or any other suitable cross-section.

Figure 15:
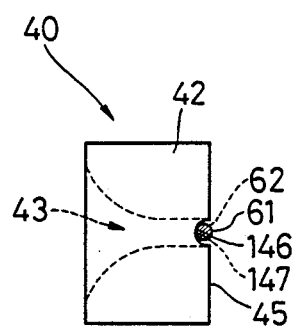
FIG. 15 is a side elevational view showing another modification of a guide member.

FIG. 15 shows a modification of the guide member 42 of the guide unit 40 illustrated in FIGS. 5 through 10. In FIG. 15, like or similar reference numerals are used to designate components or parts like or similar to those of the embodiment shown in FIGS. 5 through 10, and the detailed description of such like or similar components or parts will therefore be omitted. The guide unit 40 shown in FIG. 15 is different from the guide unit 40 shown in FIG. 5 in that a pair of grooves 146 and 147 each having a semi-circular cross-section are formed in the stopper surface 45 in substitution for the bores 46 and 47 shown in FIG. 5. The grooves 146 and 147 extend perpendicularly to the axis of the guide passage 43 and perpendicularly to the direction in which the upper staking die 30 is moved toward and away from the lower staking die 20 as described previously with reference to FIGS. 5 through 10. The aforesaid optical fibers 61 and 62 are fitted respectively into the grooves 146 and 147, to detect passage of the suture. In the arrangement employing the guide member 42 shown in FIG. 15, when feeding of the suture is obstructed midway of the guide passage 43, the suture does not intercept the light from the optical fiber 61 to the optical fiber 62, so that it can be ensured to detect abnormality of suture feeding.

What is claimed is:

1. An apparatus for attaching an end of a suture to a bore formed in a proximal end of a surgical needle and extending along an axis of the surgical needle, said apparatus comprising:

a pair of staking dies, at least one of said staking dies being movable toward and away from the other staking die;

guide means arranged adjacent a side surface of at least the other staking die, said guide means having a stopper surface with which a proximal end face of the surgical needle is engageable to position the surgical needle in a direction along the axis thereof, said guide means having a guide passage extending substantially perpendicularly to said stopper surface, for guiding the end of the suture, said guide passage having an inlet and an outlet, said outlet opening to said stopper surface in confronting relation to a space between said staking dies, said guide passage being provided with a tapered portion having a cross-sectional area decreasing toward said outlet; and positioning means for positioning the proximal end of the surgical needle in a direction perpendicular to the axis of the surgical needle so as to bring the bore in the proximal end of the surgical needle substantially into alignment with said outlet of said guide passage of said guide means.

2. A suture attaching apparatus as defined in claim 1, including a base frame, one of said staking dies being mounted on said base frame for movement relative thereto, the other staking die being fixedly mounted to said base frame, said staking dies having their respective forward ends confronted with each other, said forward ends being formed therein respectively with recesses, said recess in said forward en of said fixed staking die forming said positioning means for positioning the proximal end of the surgical needle in the direction perpendicular to the axis of the surgical needle.

3. A suture attaching apparatus as defined in claim 2, including a support mechanism for supporting said guide means, said base frame having therein an opening, said forward ends of the respective staking dies being confronted with each other through said opening, said support mechanism comprising a plurality of flanges mounted on said base frame and circumferentially spaced from each other, and a plurality of bolts threadedly engaged respectively with said flanges, said bolts having their respective forward ends abutted respectively against a plurality of planar surfaces formed on an outer periphery of said guide means, wherein adjustment in position of said bolts with respect to the respective flanges enables said guide means to be adjusted in position relative to said base frame.

4. A suture attaching apparatus as defined in claim 2, wherein said guide means has a slit permitting the suture to be taken out of said guide passage to the outside of said guide means in a direction perpendicular to an axis of the suture.

5. A suture attaching apparatus as defined in claim 2, wherein said guide means is composed of a pair of half-split components, one of said components being fixedly mounted to said base frame, said apparatus further including means for moving the other component toward and away from said one component.

6. A suture attaching apparatus as defined in claim 1, wherein said guide passage has a circular cross-sectional shape.

7. A suture attaching apparatus as defined in claim 6, wherein said outlet of said guide passage has a diameter at least equal to that of the end of the suture to be inserted into the bore in the surgical needle and at most equal to that of an open end of the bore in the surgical needle.

8. A suture attaching apparatus as defined in claim 7, wherein said tapered portion of said guide passage becomes gentler and gentler in gradient toward said outlet of said guide passage.

9. A suture attaching apparatus as defined in claim 7, wherein said guide passage has a straight portion extending through a predetermined length adjacent said outlet, said straight portion being substantially equal in diameter over the entire length, said tapered portion having a terminating end smoothly merging to said straight portion.

10. A suture attaching apparatus as defined in claim 1, wherein said guide passage is formed by a groove having a generally U-shaped cross-section.

11. A suture attaching apparatus as defined in claim 1, including suture seeding means arranged short of said guide means, for feeding the suture into said guide passage of said guide means.

12. A suture attaching apparatus as defined in claim 11, wherein said suture feeding means comprises a pair of rollers, a motor drivingly connected to one of said pair of rollers, and means for resiliently biasing the other roller toward said one roller, in which the suture is clamped between said pair of rollers and is fed thereby into the bore of the surgical needle through said guide passage of said guide means when said one roller is driven by said motor.

13. A suture attaching apparatus as defined in claim 11, including detecting means for detecting whether the suture is caused to pass through said guide passage, to output a signal representative of passage of the suture through said guide passage, and means operative in response to the signal from said detecting means to complete operation of said suture feeding means after an elapse of a predetermined time from reception of said signal from said detecting means.

14. A suture attaching apparatus as defined in claim 13, wherein said detecting means comprises a pair of first and second optical fibers, a light emitting element optically connected to one end of said first optical fiber, and a light receiving element optically connected to one end of said second optical fiber, said first and second optical fibers having their respective other ends which are aligned with each other and which are confronted with each other through said guide passage.

15. A suture attaching apparatus as defined in claim 14, wherein said guide means is formed therein with a pair of bores adjacent said outlet, said pair of bores being aligned with each other and in communication with said guide passage, the other ends of the respective optical fibers being fixedly fitted respectively into said pair of bores.

16. A suture attaching apparatus as defined in claim 14, wherein said guide means has a pair of grooves formed in said stopper surface, said pair of grooves being aligned with each other and in communication with said outlet of said guide passage, the other ends of the respective optical fibers being fixedly fitted respectively into said pair of grooves.

* * * * *

UNITED STATES PATENT AND TRADEMARK OFFICE
CERTIFICATE OF CORRECTION

PATENT NO. : 4,799,311

DATED : January 24, 1989

INVENTOR(S) : Kanji MATSUTANI

It is certified that error appears in the above-identified patent and that said Letters Patent is hereby corrected as shown below:

Claim 2, column 10, line 52, change "en" to --end--.

Claim 7, column 11, line 19, change "diameter-" to --diameter--.

Claim 11, column 11, line 42, change "sage-" to --sage--.

Signed and Sealed this

Twenty-fifth Day of July, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,799,311

DATED : January 24, 1989

INVENTOR(S) : Kanji MATSUTANI

It is certified that error appears in the above-identified patent and that said Letters Patent is hereby corrected as shown below:

Claim 11, column 11, line 40, change "seeding" to --feeding--.

Signed and Sealed this

Twenty-sixth Day of September, 1989

Attest:

DONALD J. QUIGG

Attesting Officer

Commissioner of Patents and Trademarks